United States Patent [19]

Scannon

[11] Patent Number: 5,686,414
[45] Date of Patent: Nov. 11, 1997

[54] METHODS OF TREATING CONDITIONS ASSOCIATED WITH CORNEAL TRANSPLANTATION

[75] Inventor: Patrick J. Scannon, San Francisco, Calif.

[73] Assignee: Xoma Corporation, Berkeley, Calif.

[21] Appl. No.: 557,287

[22] Filed: Nov. 14, 1995

[51] Int. Cl.⁶ .................... C07K 14/00; A61K 37/00
[52] U.S. Cl. .................... 514/12; 530/300; 530/350
[58] Field of Search .................... 514/12; 530/300, 530/350

[56] References Cited

U.S. PATENT DOCUMENTS 5,348,942  9/1994  Little et al. .................... 514/12

OTHER PUBLICATIONS

Lin et al. 1996. Antimicrobial Agents & Chemo Therapy 40: 65–69.
Saunders et al 1995 Int'l J. Antimicrobial Agents 5: 259–263.
Nikolic et al 1986 Invastigative Opthalmology and Visual Science 27: 449–456.
Boisioly et al 1981 Am J Opthalmology 107: 647–654.

*Primary Examiner*—Karen C. Carlson
*Attorney, Agent, or Firm*—McAndrews, Held & Malloy, Ltd.

[57] ABSTRACT

The present invention provides methods of treating a subject suffering from adverse effects, complications or conditions, associated with or resulting from corneal transplantation, by topical administration of suitable ophthalmic preparations of bactericidal/permeability-increasing (BPI) protein products.

9 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( i x ) FEATURE:
        ( A ) NAME/KEY: misc_feature
        ( D ) OTHER INFORMATION: "rBPI"

( x i ) SEQUENCE DESCRIPTION: SEQ ID NO:1:

```
CAGGCCTTGA  GGTTTTGGCA  GCTCTGGAGG  ATG AGA GAG AAC ATG GCC AGG GGC    54
                                    Met Arg Glu Asn Met Ala Arg Gly
```

|  |  |  |  |  |  |  |  |  | -31 | -30 |  |  |  |  | -25 |  |  |
|---|---|---|---|---|---|---|---|---|---|---|---|---|---|---|---|---|---|

```
CCT TGC AAC GCG CCG AGA TGG GTG TCC CTG ATG GTG CTC GTC GCC ATA         102
Pro Cys Asn Ala Pro Arg Trp Val Ser Leu Met Val Leu Val Ala Ile
        -20             -15                     -10

GGC ACC GCC GTG ACA GCG GCC GTC AAC CCT GGC GTC GTG GTC AGG ATC         150
Gly Thr Ala Val Thr Ala Ala Val Asn Pro Gly Val Val Val Arg Ile
        -5                   1           5

TCC CAG AAG GGC CTG GAC TAC GCC AGC CAG CAG GGG ACG GCC GCT CTG         198
Ser Gln Lys Gly Leu Asp Tyr Ala Ser Gln Gln Gly Thr Ala Ala Leu
 10              15              20                          25

CAG AAG GAG CTG AAG AGG ATC AAG ATT CCT GAC TAC TCA GAC AGC TTT         246
Gln Lys Glu Leu Lys Arg Ile Lys Ile Pro Asp Tyr Ser Asp Ser Phe
                 30              35                      40

AAG ATC AAG CAT CTT GGG AAG GGG CAT TAT AGC TTC TAC AGC ATG GAC         294
Lys Ile Lys His Leu Gly Lys Gly His Tyr Ser Phe Tyr Ser Met Asp
             45                  50                  55

ATC CGT GAA TTC CAG CTT CCC AGT TCC CAG ATA AGC ATG GTG CCC AAT         342
Ile Arg Glu Phe Gln Leu Pro Ser Ser Gln Ile Ser Met Val Pro Asn
         60                  65                  70

GTG GGC CTT AAG TTC TCC ATC AGC AAC GCC AAT ATC AAG ATC AGC GGG         390
Val Gly Leu Lys Phe Ser Ile Ser Asn Ala Asn Ile Lys Ile Ser Gly
     75                  80                  85

AAA TGG AAG GCA CAA AAG AGA TTC TTA AAA ATG AGC GGC AAT TTT GAC         438
Lys Trp Lys Ala Gln Lys Arg Phe Leu Lys Met Ser Gly Asn Phe Asp
 90              95              100                     105

CTG AGC ATA GAA GGC ATG TCC ATT TCG GCT GAT CTG AAG CTG GGC AGT         486
Leu Ser Ile Glu Gly Met Ser Ile Ser Ala Asp Leu Lys Leu Gly Ser
             110                 115                 120

AAC CCC ACG TCA GGC AAG CCC ACC ATC ACC TGC TCC AGC TGC AGC AGC         534
Asn Pro Thr Ser Gly Lys Pro Thr Ile Thr Cys Ser Ser Cys Ser Ser
         125                 130                 135

CAC ATC AAC AGT GTC CAC GTG CAC ATC TCA AAG AGC AAA GTC GGG TGG         582
His Ile Asn Ser Val His Val His Ile Ser Lys Ser Lys Val Gly Trp
         140                 145                 150

CTG ATC CAA CTC TTC CAC AAA AAA ATT GAG TCT GCG CTT CGA AAC AAG         630
Leu Ile Gln Leu Phe His Lys Lys Ile Glu Ser Ala Leu Arg Asn Lys
     155                 160                 165

ATG AAC AGC CAG GTC TGC GAG AAA GTG ACC AAT TCT GTA TCC TCC AAG         678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT         726
Leu Gln Pro Tyr Phe Gln Thr Leu Pro Val Met Thr Lys Ile Asp Ser
             190                 195                 200

GTG GCT GGA ATC AAC TAT GGT CTG GTG GCA CCT CCA GCA ACC ACG GCT         774
Val Ala Gly Ile Asn Tyr Gly Leu Val Ala Pro Pro Ala Thr Thr Ala
         205                 210                 215

GAG ACC CTG GAT GTA CAG ATG AAG GGG GAG TTT TAC AGT GAG AAC CAC         822
Glu Thr Leu Asp Val Gln Met Lys Gly Glu Phe Tyr Ser Glu Asn His
     220                 225                 230

CAC AAT CCA CCT CCC TTT GCT CCA CCA GTG ATG GAG TTT CCC GCT GCC         870
His Asn Pro Pro Pro Phe Ala Pro Pro Val Met Glu Phe Pro Ala Ala
235                 240                 245

CAT GAC CGC ATG GTA TAC CTG GGC CTC TCA GAC TAC TTC TTC AAC ACA         918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA         966
Ala Gly Leu Val Tyr Gln Glu Ala Gly Val Leu Lys Met Thr Leu Arg
             270                 275                 280

GAT GAC ATG ATT CCA AAG GAG TCC AAA TTT CGA CTG ACA ACC AAG TTC        1014
Asp Asp Met Ile Pro Lys Glu Ser Lys Phe Arg Leu Thr Thr Lys Phe
```

-continued

|  |  |  |  |  |  | 285 |  |  |  |  |  | 290 |  |  |  |  |  | 295 |  |  |  |  |
|---|---|---|---|---|---|---|---|---|---|---|---|---|---|---|---|---|---|---|---|---|---|---|---|

```
TTT  GGA  ACC  TTC  CTA  CCT  GAG  GTG  GCC  AAG  AAG  TTT  CCC  AAC  ATG  AAG        1062
Phe  Gly  Thr  Phe  Leu  Pro  Glu  Val  Ala  Lys  Lys  Phe  Pro  Asn  Met  Lys
          300            305                      310

ATA  CAG  ATC  CAT  GTC  TCA  GCC  TCC  ACC  CCG  CCA  CAC  CTG  TCT  GTG  CAG        1110
Ile  Gln  Ile  His  Val  Ser  Ala  Ser  Thr  Pro  Pro  His  Leu  Ser  Val  Gln
     315            320                      325

CCC  ACC  GGC  CTT  ACC  TTC  TAC  CCT  GCC  GTG  GAT  GTC  CAG  GCC  TTT  GCC        1158
Pro  Thr  Gly  Leu  Thr  Phe  Tyr  Pro  Ala  Val  Asp  Val  Gln  Ala  Phe  Ala
330            335                      340                           345

GTC  CTC  CCC  AAC  TCC  TCC  CTG  GCT  TCC  CTC  TTC  CTG  ATT  GGC  ATG  CAC        1206
Val  Leu  Pro  Asn  Ser  Ser  Leu  Ala  Ser  Leu  Phe  Leu  Ile  Gly  Met  His
               350                 355                      360

ACA  ACT  GGT  TCC  ATG  GAG  GTC  AGC  GCC  GAG  TCC  AAC  AGG  CTT  GTT  GGA        1254
Thr  Thr  Gly  Ser  Met  Glu  Val  Ser  Ala  Glu  Ser  Asn  Arg  Leu  Val  Gly
               365                 370                      375

GAG  CTC  AAG  CTG  GAT  AGG  CTG  CTC  CTG  GAA  CTG  AAG  CAC  TCA  AAT  ATT        1302
Glu  Leu  Lys  Leu  Asp  Arg  Leu  Leu  Leu  Glu  Leu  Lys  His  Ser  Asn  Ile
          380                 385                      390

GGC  CCC  TTC  CCG  GTT  GAA  TTG  CTG  CAG  GAT  ATC  ATG  AAC  TAC  ATT  GTA        1350
Gly  Pro  Phe  Pro  Val  Glu  Leu  Leu  Gln  Asp  Ile  Met  Asn  Tyr  Ile  Val
     395                 400                      405

CCC  ATT  CTT  GTG  CTG  CCC  AGG  GTT  AAC  GAG  AAA  CTA  CAG  AAA  GGC  TTC        1398
Pro  Ile  Leu  Val  Leu  Pro  Arg  Val  Asn  Glu  Lys  Leu  Gln  Lys  Gly  Phe
410                      415                 420                      425

CCT  CTC  CCG  ACG  CCG  GCC  AGA  GTC  CAG  CTC  TAC  AAC  GTA  GTG  CTT  CAG        1446
Pro  Leu  Pro  Thr  Pro  Ala  Arg  Val  Gln  Leu  Tyr  Asn  Val  Val  Leu  Gln
               430                      435                      440

CCT  CAC  CAG  AAC  TTC  CTG  CTG  TTC  GGT  GCA  GAC  GTT  GTC  TAT  AAA             1491
Pro  His  Gln  Asn  Phe  Leu  Leu  Phe  Gly  Ala  Asp  Val  Val  Tyr  Lys
               445                      450                 455

TGAAGGCACC AGGGGTGCCG GGGGCTGTCA GCCGCACCTG TTCCTGATGG GCTGTGGGGC                     1551

ACCGGCTGCC TTTCCCCAGG GAATCCTCTC CAGATCTTAA CCAAGAGCCC CTTGCAAACT                     1611

TCTTCGACTC AGATTCAGAA ATGATCTAAA CACGAGGAAA CATTATTCAT TGGAAAAGTG                     1671

CATGGTGTGT ATTTAGGGA  TTATGAGCTT CTTTCAAGGG CTAAGGCTGC AGAGATATTT                     1731

CCTCCAGGAA TCGTGTTTCA ATTGTAACCA AGAAATTTCC ATTTGTGCTT CATGAAAAAA                     1791

AACTTCTGGT TTTTTCATG  TG                                                             1813
```

( 2 ) INFORMATION FOR SEQ ID NO:2:

( i ) SEQUENCE CHARACTERISTICS:
      ( A ) LENGTH: 487 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met  Arg  Glu  Asn  Met  Ala  Arg  Gly  Pro  Cys  Asn  Ala  Pro  Arg  Trp  Val
-31       -30                 -25                 -20

Ser  Leu  Met  Val  Leu  Val  Ala  Ile  Gly  Thr  Ala  Val  Thr  Ala  Ala  Val
-15            -10                 -5                                     1

Asn  Pro  Gly  Val  Val  Val  Arg  Ile  Ser  Gln  Lys  Gly  Leu  Asp  Tyr  Ala
               5                 10                      15

Ser  Gln  Gln  Gly  Thr  Ala  Ala  Leu  Gln  Lys  Glu  Leu  Lys  Arg  Ile  Lys
          20                 25                      30

Ile  Pro  Asp  Tyr  Ser  Asp  Ser  Phe  Lys  Ile  Lys  His  Leu  Gly  Lys  Gly
     35                 40                      45
```

-continued

| | | | | | | | | | | | | | | |
|---|---|---|---|---|---|---|---|---|---|---|---|---|---|---|
| His | Tyr | Ser | Phe | Tyr | Ser | Met | Asp | Ile | Arg | Glu | Phe | Gln | Leu | Pro | Ser |
| 50 | | | | | 55 | | | | | 60 | | | | | 65 |
| Ser | Gln | Ile | Ser | Met | Val | Pro | Asn | Val | Gly | Leu | Lys | Phe | Ser | Ile | Ser |
| | | | | 70 | | | | | 75 | | | | | 80 | |
| Asn | Ala | Asn | Ile | Lys | Ile | Ser | Gly | Lys | Trp | Lys | Ala | Gln | Lys | Arg | Phe |
| | | | | 85 | | | | | 90 | | | | | 95 | |
| Leu | Lys | Met | Ser | Gly | Asn | Phe | Asp | Leu | Ser | Ile | Glu | Gly | Met | Ser | Ile |
| | | | 100 | | | | | 105 | | | | | 110 | | |
| Ser | Ala | Asp | Leu | Lys | Leu | Gly | Ser | Asn | Pro | Thr | Ser | Gly | Lys | Pro | Thr |
| | | | 115 | | | | 120 | | | | | 125 | | | |
| Ile | Thr | Cys | Ser | Ser | Cys | Ser | Ser | His | Ile | Asn | Ser | Val | His | Val | His |
| 130 | | | | | 135 | | | | | 140 | | | | | 145 |
| Ile | Ser | Lys | Ser | Lys | Val | Gly | Trp | Leu | Ile | Gln | Leu | Phe | His | Lys | Lys |
| | | | | 150 | | | | | 155 | | | | | 160 | |
| Ile | Glu | Ser | Ala | Leu | Arg | Asn | Lys | Met | Asn | Ser | Gln | Val | Cys | Glu | Lys |
| | | | 165 | | | | | 170 | | | | | 175 | | |
| Val | Thr | Asn | Ser | Val | Ser | Ser | Lys | Leu | Gln | Pro | Tyr | Phe | Gln | Thr | Leu |
| | | | 180 | | | | | 185 | | | | | 190 | | |
| Pro | Val | Met | Thr | Lys | Ile | Asp | Ser | Val | Ala | Gly | Ile | Asn | Tyr | Gly | Leu |
| | | | 195 | | | | 200 | | | | | 205 | | | |
| Val | Ala | Pro | Pro | Ala | Thr | Thr | Ala | Glu | Thr | Leu | Asp | Val | Gln | Met | Lys |
| 210 | | | | | 215 | | | | | 220 | | | | | 225 |
| Gly | Glu | Phe | Tyr | Ser | Glu | Asn | His | His | Asn | Pro | Pro | Pro | Phe | Ala | Pro |
| | | | | 230 | | | | | 235 | | | | | 240 | |
| Pro | Val | Met | Glu | Phe | Pro | Ala | Ala | His | Asp | Arg | Met | Val | Tyr | Leu | Gly |
| | | | 245 | | | | | 250 | | | | | 255 | | |
| Leu | Ser | Asp | Tyr | Phe | Phe | Asn | Thr | Ala | Gly | Leu | Val | Tyr | Gln | Glu | Ala |
| | | | 260 | | | | | 265 | | | | | 270 | | |
| Gly | Val | Leu | Lys | Met | Thr | Leu | Arg | Asp | Asp | Met | Ile | Pro | Lys | Glu | Ser |
| | | | 275 | | | | | 280 | | | | | 285 | | |
| Lys | Phe | Arg | Leu | Thr | Thr | Lys | Phe | Phe | Gly | Thr | Phe | Leu | Pro | Glu | Val |
| 290 | | | | | 295 | | | | | 300 | | | | | 305 |
| Ala | Lys | Lys | Phe | Pro | Asn | Met | Lys | Ile | Gln | Ile | His | Val | Ser | Ala | Ser |
| | | | | 310 | | | | | 315 | | | | | 320 | |
| Thr | Pro | Pro | His | Leu | Ser | Val | Gln | Pro | Thr | Gly | Leu | Thr | Phe | Tyr | Pro |
| | | | 325 | | | | | 330 | | | | | 335 | | |
| Ala | Val | Asp | Val | Gln | Ala | Phe | Ala | Val | Leu | Pro | Asn | Ser | Ser | Leu | Ala |
| | | | 340 | | | | | 345 | | | | | 350 | | |
| Ser | Leu | Phe | Leu | Ile | Gly | Met | His | Thr | Thr | Gly | Ser | Met | Glu | Val | Ser |
| | | | 355 | | | | | 360 | | | | | 365 | | |
| Ala | Glu | Ser | Asn | Arg | Leu | Val | Gly | Glu | Leu | Lys | Leu | Asp | Arg | Leu | Leu |
| 370 | | | | | 375 | | | | | 380 | | | | | 385 |
| Leu | Glu | Leu | Lys | His | Ser | Asn | Ile | Gly | Pro | Phe | Pro | Val | Glu | Leu | Leu |
| | | | | 390 | | | | | 395 | | | | | 400 | |
| Gln | Asp | Ile | Met | Asn | Tyr | Ile | Val | Pro | Ile | Leu | Val | Leu | Pro | Arg | Val |
| | | | 405 | | | | | 410 | | | | | 415 | | |
| Asn | Glu | Lys | Leu | Gln | Lys | Gly | Phe | Pro | Leu | Pro | Thr | Pro | Ala | Arg | Val |
| | | | 420 | | | | | 425 | | | | | 430 | | |
| Gln | Leu | Tyr | Asn | Val | Val | Leu | Gln | Pro | His | Gln | Asn | Phe | Leu | Leu | Phe |
| | | | 435 | | | | | 440 | | | | | 445 | | |
| Gly | Ala | Asp | Val | Val | Tyr | Lys | | | | | | | | | |
| 450 | | | | | 455 | | | | | | | | | | |

METHODS OF TREATING CONDITIONS ASSOCIATED WITH CORNEAL TRANSPLANTATION

BACKGROUND OF THE INVENTION

The present invention relates generally to methods of treating a subject suffering from adverse effects, complications or conditions, associated with or resulting from corneal transplantation, by topical administration of bactericidal/permeability-increasing (BPI) protein products.

Corneal transplantation or corneal grafting, also referred to as keratoplasty, is a surgical procedure in which abnormal host tissue is replaced by healthy donor corneal tissue. The graft may be partial thickness (lamellar) or full thickness (penetrating). There are optical, tectonic, therapeutic and cosmetic indications for such a procedure. Optical indications are primarily improvement of visual acuity by replacing opaque corneal tissue with clear donor tissue. Common indications include pseudophakic bullous keratopathy, keratoconus, corneal dystrophies and degenerations, and scarring caused by various types of keratitis and trauma. Tectonic indications include restoration or preservation of corneal anatomy in eyes displaying severe structural changes such as stromal thinning and descemetoceles. Therapeutic indications include removal of inflamed corneal tissue in eyes unresponsive to conventional antimicrobial or antiviral therapy. Cosmetic indications include improvement of the appearance of the eye.

Corneal transplantation is the most common form of organ transplantation performed. Transplant remains the treatment of choice for patients whose corneas are deeply scarred, extremely distorted, or afflicted with dystrophies of the deep corneal layers. The number of corneal transplants in the U.S. has increased dramatically since 1980 from 14,400 to 28,926 in 1985, then to 40,631 in 1990, and in 1994 to 43,743, according to the Eye Bank Association of America. As of Dec. 31, 1994, nearly 7,000 people were waiting for a donor cornea.

Adverse prognostic factors for corneal transplant include: severe stromal vascularization, absence of corneal sensation, extreme thinning at the proposed host-graft junction and active corneal inflammation. Associated adverse factors which may diminish the prognosis of obtaining a clear graft after transplantation operation include: uncontrolled glaucoma, anterior synechiae, uveitis, and recurrent or progressive forms of conjunctival inflammation, such as acne rosacea and ocular cicatricial pemphigoid. In general, the most favorable prognosis attaches to transplants effected in response to localized corneal scars, keratoconus and cornea/dystrophies.

As in other solid tissue transplants, immunologic rejection can sometimes severely limit the success of this procedure. Generally, the cornea has been viewed as a "privileged" site for transplantation and animal experiments have established that donor tissue can persist in the host cornea for long periods of time, as long as the host cornea remains avascular. Lack of post-surgical vascularization ("neovascularization") in the recipient has been established as a primary indicator of long term acceptance of a corneal graft.

Despite the generally avascular state of the normal cornea, corneal grafts are rejected at a significant rate necessitating therapeutic intervention. Graft rejection is commonly defined as cessation of function of the transplant caused by immunological reactions. The incidence of graft reaction varies, among other things, with the pathological status or disease of the host cornea, ocular irritation by external physical agents or concomitant infectious disease. Cornea/graft rejection has been reported to vary from 12–13% in good prognosis cases (mostly avascular corneas). Other reports indicate rejection occurs in 2.3% to 35% of cases when the recipient's cornea is avascular. When the recipient's cornea is heavily vascularized, however, rejection has been reported to occur in up to 65% of cases, with about 50% of these grafts ultimately failing.

It has been shown experimentally that the growth of blood vessels into the cornea usually brings along new lymphatic capillaries. The combination of blood vessels and lymphatic channels opens the door for antigen release from the otherwise immunoprotected cornea and for immunocompetent cells to reach the corneal graft. Thus, immune graft reaction will vary with the condition of the recipient cornea (e.g., scarring, vascularization, active inflammation, previous grafts and other factors), the immunologic status of the host and a multitude of noncorneal conditions which may facilitate and accelerate graft reactions (e.g., dry eyes, lid closure defects, glaucoma, etc.). These conditions are thought to play vital roles, especially in the early post-operative period, and thought to partially explain the severity of early rejection. In addition to the status of the host, surgical technique and particularly problems with suturing and wound healing may increase the incidence of adverse effects or reactions after corneal transplant.

In the cornea, graft rejection is characterized by a progressive clouding of the corneal transplant in the absence of other trauma or ocular disease and a reasonable clinical diagnosis of corneal graft rejection can be made if a corneal transplant was clear prior to an episode of opacification. It is well recognized that the rejection process can involve any single layer of cornea or all layers at the same time. The clinical picture of rejection in each layer is so distinctive as to be almost diagnostic. Experimental studies of epithelial, stromal or endothelial rejection have uniformly indicated participation of lymphocytes in the rejection process.

Current therapies for preventing or treating rejection and its associated conditions or complications have been limited principally to administration of immunosuppressant corticosteroids. In fact, topical corticosteroids have been the mainstay of therapy in the prevention and treatment of corneal allograft rejection in humans and treatment is generally started immediately after corneal transplant surgery. A great deal of individual variation exists with respect to the specifics of postoperative corticosteroid therapy. Steroids are sometimes continued anti the time of suture removal, while some clinicians continue topical therapy in small doses for 1 or more years (sometimes indefinitely). Patients must be alerted to the earliest symptoms of graft rejection. For "mild" signs of rejection it may be sufficient to administer topical steroids every 3 hours with careful follow-up every second day to monitor the effect. In such cases, treatment would likely be administered for at least 3 weeks before deciding that a graft is irreversibly edematous. Alternatively, intensive local corticosteroid treatment may be given early in the course of a reaction. This usually consists of hourly applications of topical steroids and even periocular injections of depot preparations.

Unfortunately, steroid therapy engenders its own set of complications and risks. In particular, ocular toxicity and localized side effects of corticosteroids present significant problems. For example, topical corticosteroids can cause ocular hypertension or cataracts, enhance secondary bacterial, fungal or vital infections of the ocular surface due to localized immune suppression, or inhibit corneal epithelial and stromal healing both in post-operative therapy and in association with epithelial and stromal defects. In particular, it is well documented that corticosteroids may predispose a graft to microbial infection or influence the clinical course of these infections. In one study, 68–100% of patients developing microbial keratitis in grafts were reportedly using topical corticosteroid drops at the time the infection occurred. It is known that corticosteroid drops specifically impair the local host-defense mechanisms allowing infections to flourish. Further, as corticosteroid therapy of infected grafts is tapered off or discontinued, an increased inflammatory reaction can often be expected.

In cases of infection associated with steroid therapy following transplantation, chronic topical antibiotic administration may allow resistant organisms to emerge and affect the development and course of microbial keratitis following transplant. In one study, 95% of organisms causing microbial keratitis in transplants were resistant to the antibiotic the patient was currently using. Thus, microbial infection of a corneal transplant has become a complication that is a bane to transplant practitioners. The incidence of microbial keratitis following penetrating keratoplasty in the United States has been reported to range from 1.8–4.9%. The visual sequelae of this complication can be devastating. In one study, a reduction in visual acuity was noted to occur in 46% of the eyes that had a graft infection. In another study, visual acuity better than 20/200 was achieved in only 14% of infected cases. A third study found that only 40% of previously clear grafts remained clear following treatment for microbial infection. Although the complication of infection can occur at any time following surgery, one study found that 55% and another found that 88% of graft infections occurred less than 1 year after surgery.

Means of preventing graft rejection without involvement of steroids and/or chronic administration of antibiotics are continually being investigated, but thus far have met with little success. Drugs such as antilymphocyte serum and azathioprine have been used experimentally, but in general have been considered too dangerous for routine use in clinical situations. While immunologic manipulation of the host and donor tissues may hold promise for improved success in corneal grafting, other, nonimmunologic approaches are being pursued as well, including improved surgical techniques, better methods of examining the donor endothelium, and long-term storage of corneal tissue.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979) ] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 1 hereto.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.*, 262:14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et al., *Infect. Immun.* 60:4754–4761 (1992).

There remains a need in the art for therapies for the pre- and post-operative treatment of corneal transplant patient in both normal and high-risk (e.g., vascularized cornea) populations and effective to prevent or treat corneal graft rejection, post-transplant neovascularization and corneal opacification without the potential side effects, toxicities, complications or risks associated with corticosteroid therapy. Such therapies would most preferably involve localized, rather than systemic, treatment with agents capable of penetrating corneal tissue and therapeutic materials would advantageously be applicable to donor tissues prior to transplantation. In addition, therapies that would ideally provide antimicrobial protection (alone or as an adjunct to treatment with antimicrobial agents such as antibiotics).

SUMMARY OF THE INVENTION

The present invention provides novel methods for treating corneal transplant patients through topical administration to the cornea of the patient of a bactericidal/permeability-increasing (BPI) product in an mount effective to reduce the incidence of transplant rejection or of corneal neovascularization and/or corneal opacification. Presently preferred BPI protein products for practice of the invention include biologically active amino terminal fragments of the BPI holoprotein, recombinant products such as rBPI$_{21}$ and rBPI$_{42}$ and recombinant or chemically synthesized BPI-derived peptides as described in detail below.

Methods of the present invention contemplate administration of a BPI protein product in ophthalmologically acceptable preparations which may include, or be concurrently administered with, anti-inflammatory agents such as corticosteroids and/or antimicrobial agents including anti-bacterial agents such as ciprofloxacin, gentamicin and ofloxacin.

It is within the contemplation of the invention to reduce the incidence of corneal graft rejection, neovascularization and/or corneal opacification in corneal transplant patients by pre- and post-operative application of BPI protein products to the eye of the patient as well as by pre-operative application to the corneal tissue to be engrafted into the eye of the recipient.

Practice of the invention is expected to provide for reduction, through prevention or alleviation, of one or more adverse effects and symptoms commonly noted in corneal transplantation patients including formation of characteristic epithelial and endothelial rejection bands or lines, photophobia, hyperemia, chemosis, iritis, changes in intraocular pressure (IOP), loss of visual acuity and ocular pain. Practice of the invention is expected to reduce the incidence of microbial infection and hence accelerate healing at the graft site.

Numerous aspects and advantages of the present invention will become apparent upon consideration of the following detailed description of preferred embodiments thereof.

DETAILED DESCRIPTION

Incorporated by reference herein are the disclosures of the applicant's co-owned, co-pending, concurrently-filed U.S. patent application Ser. No. 08/557,289 (Attorney Docket No. 27129/33006) entitled "Methods of Treating Conditions Associated With Corneal Injury."

The present invention relates to the surprising discovery that a BPI protein product can be topically administered to a corneal transplant patient in an amount effective to reduce the incidence (i.e., occurrence or severity) of transplant rejection, corneal neovascularization or corneal opacification. Methods according to the invention are useful for treating subjects suffering from adverse effects, complications or conditions associated with or resulting from corneal transplantation, including graft rejection, neovascularization and/or opacification of the corneal graft and provides methods of preventing or treating such conditions. Particularly valuable is the lack of corneal tissue toxicity and the effectiveness of such topically administered BPI protein products, given that penetration of corneal tissue is a necessary but not sufficient step for therapeutic efficacy. BPI protein products are established herein to prevent or reduce adverse effects associated with corneal transplantation, including graft rejection, infection, ulceration, or injury, as measured by examination, using, for example, slit lamp biomicroscopy to note clinical manifestations of graft rejection, infection, ulceration or injury.

According to an aspect of the invention, suitable ophthalmic preparations of BPI protein product alone, in an amount sufficient for monotherapeutic effectiveness, may be administered to a corneal transplant patient. When used to describe administration of BPI protein product alone, the term "amount sufficient for monotherapeutic effectiveness" means a suitable ophthalmic preparation having an amount of BPI protein product that provides beneficial effects, including anti-angiogenic and/or antimicrobial effects, when administered as a monotherapy. The invention utilizes any of the large variety of BPI protein products known to the art including natural BPI protein isolates, recombinant BPI protein, BPI fragments, BPI analogs, BPI variants, and BPI-derived peptides.

According to another aspect of the invention, a corneal transplant patient may be treated by concurrent (together, before or after) administration of suitable ophthalmic preparations of a BPI protein product in an amount sufficient for combinative therapeutic effectiveness and one or more immunosuppressant corticosteroids in amounts sufficient for combinative therapeutic effectiveness. This aspect of the invention contemplates concurrent administration of BPI protein product with any corticosteroid or combinations of corticosteroids, including prednisolone and dexamethasone and contemplates that, where corticosteroid therapy is required, lesser amounts will be needed and/or that there will be a reduction in the duration of treatment.

According to another aspect of the invention, a corneal transplant patient may be treated by concurrent administration of suitable ophthalmic preparations of a BPI protein product in an amount sufficient for combinative therapeutic effectiveness and one or more antimicrobial agents in amounts sufficient for combinative therapeutic effectiveness. This aspect of the invention contemplates concurrent administration of BPI protein product with any antimicrobial agent or combinations thereof for topical use in the eye including: antibacterial agents such as gentamicin, tobramycin, bacitracin, chloramphenicol, ciprofloxacin, ofloxaein, norfloxacin, erythromycin, bacitracin/neomyein/polymyxin B, sulfisoxazole, sulfacetamide, tetracycline, polymyxin/ bacitracin, trimethroprim/polymyxin B, vancomyein, clindamycin, ticarcillin, penicillin, oxacillin or cefazolin; antifungal agents such as amphotericin B, nystatin, natamycin (pimaricin), miconazole, ketocanozole or fluconazole; antiviral agents such as idoxuridine, vidarabine or trifluridine; and antiprotozoal agents such as propamidine, neomycin, clotrimazol, miconazole, itraconazole or polyhexamethylene biguanide.

This aspect of the invention is based on the improved therapeutic effectiveness of suitable ophthalmic preparations of BPI protein products with antimicrobial agents, e.g., by providing anti-angiogenic activity in conjunction with antimicrobial activity, by increasing the antimicrobial susceptibility of infecting organisms to a reduced dosage of antimicrobials providing benefits in reduction of cost of antimicrobial therapy and/or reduction of risk of toxic responses to antimicrobials. BPI protein products may lower the minimum concentration of antimicrobials needed to inhibit in vitro growth of organisms at 24 hours. In cases where BPI protein product does not affect growth at 24 hours, BPI protein product may potentiate the early microbicidal effect of the agents in vitro at 0–7 hours. The BPI protein products may exert these effects even on organisms that are not susceptible to the direct microbicidal or growth inhibitory effects of BPI protein product alone.

This aspect of the invention is correlated to effective reversal of the antimicrobial resistance of an organism by administration of a BPI protein product and antimicrobial. BPI protein products may reduce the minimum inhibitory concentration of antimicrobials from a level within the clinically resistant range to a level within the clinically susceptible range. BPI protein products thus may convert normally antimicrobial-resistant organisms into antimicrobial-susceptible organisms.

According to these aspects of the invention, suitable ophthalmic preparations of the BPI protein product along with corticosteroids and/or antibiotics are concurrently administered in amounts sufficient for combinative therapeutic effectiveness. When used to describe administration of a suitable ophthalmic preparation of BPI protein product in conjunction with a corticosteroid, the term "amount sufficient for combinative therapeutic effectiveness" with respect to the BPI protein product means at least an amount effective to reduce or minimize neovascularization and/or increase or enhance graft survival, and the term "amount sufficient for combinative therapeutic effectiveness" with respect to a corticosteroid means at least an amount of the corticosteroid that reduces or minimizes inflammation and/ or increases or enhances graft survival when administered in conjunction with that amount of BPI protein product. Either the BPI protein product or the corticosteroid, or both, may be administered in an amount below the level required for monotherapeutic effectiveness against adverse effects associated with or resulting from corneal transplantation. When used to describe administration of a suitable ophthalmic preparation of BPI protein product in conjunction with an antimicrobial, the term "amount sufficient for combinative therapeutic effectiveness" with respect to the BPI protein product means at least an amount effective to reduce neovascularization and/or increase the susceptibility of the organism to the antimicrobial, and the term "amount sufficient for combinative therapeutic effectiveness" with respect to an antimicrobial means at least an amount of the antimicrobial that produces bactericidal or growth inhibitory effects when administered in conjunction with that amount of BPI protein product. Either the BPI protein product or the antimicrobial, or both, may be administered in an amount below the level required for monotherapeutic effectiveness against adverse effects associated with or resulting from corneal transplantation.

BPI protein product may be administered in addition to standard therapy and is preferably incorporated into the initial care given the corneal transplant patient. The BPI protein product is preferably administered topically to the patient prophylactically or as soon as possible after transplantation. Treatment with BPI protein product is preferably continued for at least 1 to 30 days, and potentially longer if necessary, in dosage amounts (e.g., dropwise administration of from about 10 to about 200 µL of a solution of the BPI protein product at about i to about 2 mg/mL) determined by good medical practice based on the clinical condition of the individual patient. BPI protein product treatment may provide the greatest benefit to high-risk patients, for example, those with vascularized corneas prior to transplantation, and additionally to those who develop serious or moderate corneal infections, ulceration or injuries following corneal transplantation, but may improve the condition of patients with any degree of corneal rejection, infection, ulceration or injury. Improvement of the patient's condition may be monitored over time as measured by preventing or reducing the development of adverse effects and symptoms commonly noted in corneal transplantation patients.

It is also within the contemplation of the invention that BPI protein products be applied to the donor corneal graft tissue prior to implantation, especially where application of ophthalmic preparations is part of pre-transplant therapy for projected transplant recipients.

Suitable ophthalmic preparations of BPI protein products may provide benefits as a result their ability to neutralize heparin and their ability to inhibit heparin-dependent angiogenesis. The anti-angiogenic properties of BPI have been described in Little et al., co-owned, co-pending U.S. application Ser. No. 08/435,855 and co-owned U.S. Pat. No. 5,348,942, both incorporated by reference herein.

Suitable ophthalmic preparations of BPI protein products may provide additional benefits as a result their ability to neutralize endotoxin associated with gram-negative bacteria and/or endotoxin released by antibiotic treatment of patients with corneal infection/ulceration. Suitable ophthalmic preparations of BPI protein products could provide further benefits due to their anti-bacterial activity against susceptible bacteria and fungi, and their ability to enhance the therapeutic effectiveness of antibiotics and anti-fungal agents. See, e.g., Horwitz et al., co-owned, co-pending U.S. application Ser. No. 08/372,783, filed Jan. 13, 1995 as a continuation-in-part of U.S. application Ser. No. 08/274,299, filed Jul. 11, 1994, which are all incorporated herein by reference and which describe BPI protein product activity in relation to gram-positive bacteria; and Little et al., co-owned, co-pending U.S. application Ser. No. 08/372,105, filed Jan. 13, 1995 as a continuation-in-part of U.S. application Ser. No. 08/273,540, filed Jul. 11, 1994, which are all incorporated herein by reference and which describe BPI protein product activity in relation to fungi.

For ophthalmic uses as described herein, the BPI protein product is preferably administered topically, to the corneal surface. The BPI protein product may be additionally administered systemically. Topical routes include administration preferably in the form of ophthalmic drops, ointments, gels or salves. Other topical routes include irrigation fluids (for, e.g., irrigation of wounds). Those skilled in the art can readily optimize effective ophthalmic dosages and administration regimens for the BPI protein products.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding and methods for expression of BPI proteins including recombinant BPI holoprotein, referred to as $rBPI_{50}$ or $rBPI_{55}$ and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et al., *J. Exp. Med.*, 174:649 (1991), and the recombinant expression product of DNA encoding N-terminal amino acids from 1 to about 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein has also been produced having the sequence (SEQ ID NOS: 1 and 2) set out in FIG. 1 of Gray et al., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 5,447,913, the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064,693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, co-owned, U.S. Pat. No. 5,420,019 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 (particularly preferred) or 199 of the N-terminal amino acids of BPI holoprotein, but wherein the cysteine at residue number 132 is substituted with alanine and is designated $rBPI_{21}\Delta cys$ or $rBPI_{21}$. Other examples include dimeric forms of BPI analogs; e.g. co-owned and co-pending U.S. patent application Ser. No. 08/212,132 filed Mar. 11, 1994, the disclosures of which are incorporated herein by reference.

Other BPI protein products useful according to the methods of the invention are peptides derived from or based on BPI produced by synthetic or recombinant means (BPI-derived peptides), such as those described in PCT Application No. US95/09262 filed Jul. 20, 1995 corresponding to co-owned and copending U.S. application Ser. No. 08/504,841 filed Jul. 20, 1995, PCT Application No. US94/10427 filed Sep. 15, 1994, which corresponds to U.S. patent application Ser. No. 08/306,473 filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993, the disclosures of all of which are incorporated herein by reference.

The safety of BPI protein products for systemic administration to humans has been established healthy volunteers and in human experimental endotoxemia studies published in von der Möhlen et al., *Blood*, 85(12):3437–3443 (1995) and von der Möhlen et al., *J. Infect. Dis.*, 172:144–151 (1995).

Presently preferred BPI protein products include recombinantly-produced N-terminal fragments of BPI, especially those having a molecular weight of approximately between 21 to 25 kD such as $rBPI_{21}$ or $rBPI_{23}$; or dimeric forms of these N-terminal fragments (e.g., $rBPI_{42}$ dimer). Additional BPI protein products include $rBPI_{55}$ and BPI-derived peptides. Presently most preferred is the $rBPI_{21}$ protein product, formulated with anti-bacterial activity-enhancing poloxamer surfactants such as Pluronic P123 (poloxamer 403) (BASF Wyandotte, Parsippany, N.J.).

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known antimicrobial agents. Pharmaceutical compositions containing BPI protein products comprise $rBPI_{21}$ at a concentration of 2 mg/ml in 5 mM citrate, 150 mM NaCl, 0.2% Pluronic P123 (poloxamer 403) or 0.2% Pluronic P103 (poloxamer 333) and 0.002% polysorbate 80. Comparisons of BPI protein product and anti-bacterial activity-enhancing poloxamer surfactants are described in co-owned, co-pending U.S. patent application Ser. Nos. 08/372,104 filed Jan. 13, 1995 and 08/530,599 filed Sep. 19, 1995 the disclosures of which are incorporated herein by reference. Another pharmaceutical composition containing a BPI protein product such as $rBPI_{21}$ comprises the BPI protein product at a concentration of 2 mg/ml in 5 mM citrate, 150 mM NaCl, 0.2% Pluronic F 68 (poloxamer 188) and 0.002% polysorbate 80. Yet another pharmaceutical composition containing a BPI protein product (e.g., $rBPI_{55}$, $rBPI_{42}$, $rBPI_{23}$) comprises the BPI protein product at a concentration of 1 mg/ml in titrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, De.). Such combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Other aspects and advantages of the present invention will be understood upon consideration of the following illustrative examples. Example 1 addresses the effects of BPI protein product administration in a corneal allograft transplantation rabbit model either alone or concurrently with corticosteroids and/or various antibiotics. Example 2 addresses the effects of BPI protein product administration in a corneal xenograft transplantation rabbit model either alone and in co-administration with corticosteroids and/or various antibiotics.

EXAMPLE 1

Effect Of BPI Protein Product Administration In A Corneal Allograft Transplantation Rabbit Model The effect of BPI protein product administration on allograft rejection is evaluated in a corneal transplantation allogenic rabbit model when administered alone or concurrently with a topical corticosteroid and/or antimicrobial agent.

For these experiments, the animals used are New Zealand White rabbits (Pine Acres Rabbitry, West Brattleboro, Vt.), and are maintained in rigid accordance to both SERI guidelines and the ARVO Resolution on the Use of Animals in Research. One eye is randomly assigned to receive the corneal graft. Rabbits weighing between 2.0 and 3.0 kg are anesthetized by intramuscular injection of 0.5–0.7 mL/kg rodent cocktail (100 mg/mL ketamine, 20 mg/mL xylazine, and 10 mg/mL acepromazine). Topical anaesthetic drops of proparacaine hydrochloride (0.5% Ophthaine, Bristol-Myers Squibb) are instilled into the animals eye together with drops of cyclopentolate (1%, Cyclogyl®, Alcon, Ft. Worth, Tex.) and phenylephrine (10.0%, CibaVision, Duluth, Ga.) to achieve maximal dilation of the pupil. One milliliter of heparin (5000 units/mL) is given intravenously to each animal in order to prevent clotting of the secondary aqueous. All operations are performed under an operating microscope.

For these experiments, donor corneas are obtained from Dutch rabbits weighing between 2.0 and 3.0 kg. Rabbits are sacrificed via a lethal intravenous dose of sodium pentobarbital (6 grs/mL, somlethol, J. A. Webster, Sterling, Mass.). Eyes are enucleated within 24 hours, stored in a modified tissue-culture medium at 4° C. Immediately preceding the corneal grafts, corneas are excised with sterile scissors and washed with the modified tissue-culture medium. For some experimental procedures, the tissue culture medium is supplemented with a BPI protein product, for pretreatment of the donor tissue prior to transplantation. Corneal buttons that are 6.25 mm are taken by trephination for grafting.

For the transplantation operation, following fixation of the eye by means of 4-0 silk sutures to 2 recti muscles, a 6 mm trephine is used to perform a partial penetrating keratoplasty placed eccentrically in the upper temporal quadrant of the cornea of each animal. The graft is positioned in such a way that a 1–2 mm margin of host cornea is visible at the point where the graft comes nearest to the limbus. After the anterior chamber is entered with the trephine, the incision is completed with corneal scissors. The corneal discs are then interchanged and held in place initially with 4 interrupted 10-0 monofilament nylon sutures which are removed at the end of the operation. A continuous 10-0 monofilament nylon suture is then used to secure the graft with the knot placed on the side of the graft nearest the limbus in order to encourage vascularization, with no attempt to bury the knot. At the end of the procedure, chloramphenicol ointment is placed on the operated eye. Alternatively, or as an adjunct to chloramphenicol a BPI protein product ophthalmic solution is applied to the recipient's eye pre- and/or post-operation. Autographs are performed in an identical manner except that the discs are sutured back into the same animal.

Postoperatively, all animals receive atropine drops (1%, Atropine sulfate, Bausch & Lomb, Tampa, Fla.) and chloramphenicol ointment (1.0%, Bausch & Lomb, Tampa, Fla.) daily until the removal of the corneal suture on day 14. On the first postoperative day, slit-lamp examination is performed noting the clarity of the graft and host cornea, anterior chamber depth and reaction, extent of corneal/iris adhesions, and any evidence of lens damage. Subsequent daily slit-lamp examinations are performed to assess the rate of the clearing of the graft, the progression of the vascularization, and any evidence of uveitis or allograft reaction.

In one study, 4 groups of rabbits undergoing allograft procedures are treated as follows: (a) 5 rabbits receive a BPI protein product 5 times daily for a minimum of 1 month; (b) 5 rabbits receive vehicle control 5 times daily for a minimum of 1 month; (c) 5 rabbits receive prednisolone (1%, Predforte®, Allergan, Irvine, Calif.) 5 times daily for a minimum of 1 month; and (d) 5 rabbits receive a BPI protein product and 1% prednisolone, each 5 times daily for a minimum of 1 month. In collateral experiments, pretreatment of the graft tissue with a BPI protein product ophthalmic solution is performed prior to implantation. Additionally, a BPI protein product ophthalmic solution is applied to irrigate the pocket and to the operated eye immediately following the operation, alone or as an adjunct to an antimicrobial agent such as chloramphenicol.

The appearance of one or more of the following clinical signs is used to indicate the onset of the allograft reaction: (1) the clouding of a part or all of the corneal stroma in a graft which had previously been clear; (2) epithelial rejection line; (3) endothelial rejection line, or (4) neovascularization which is graphed with respect to the affected corneal meridians. Graft survival is recorded in days from the date of surgery until the first day on which any of the listed clinical signs first appear. The progression of the allograft reaction is observed for several days prior to sacrificing the animal in order to confirm the diagnosis. Rabbits are sacrificed via a lethal dose of sodium pentobarbital (6 grs/mL, somelethol, J. A. Webster, Sterling, Mass.). Globes are enucleated and fixed in half-strength Karnovsky's fixative. Sections are stained with hematoxylin and eosin to determine cellular infiltration. Graft rejection scores are analyzed using the Mann-Whitney U test; statistics are performed using Statview SE+Graphics Software (Abicus Concepts, Berkeley, Calif.).

Clinical benefit of administration of BPI protein product with and without co-treatment with corticosteroids is assessed by any delay in the onset of or prevention of clinical signs of allograft reaction or rejection, delay or prevention of cornea/neovascularization and/or opacification. Clinical benefit is also assessed by reduction, through prevention or alleviation, of one or more adverse effects and symptoms associated with or resulting from corneal transplantation, including formation of characteristic epithelial or endothelial rejection lines, loss of visual acuity, photophobia, hyperemia, chemosis, iritis, changes in IOP or ocular pain.

EXAMPLE 3

Effect Of BPI Protein Product Administration In A Corneal Xenograft Transplantation Model The effect of BPI protein product administration is evaluated in a corneal xenograft transplantation model when administered alone or in combination with a topical corticosteroid and/or antimicrobial agent.

For these experiments, the animals used are New Zealand White rabbits (Pine Acres Rabbitry, West Brattleboro, Vt.), and are maintained in rigid accordance to both SERI guidelines and the ARVO Resolution on the Use of Animals in Research. One eye is randomly assigned to receive the corneal graft. Rabbits weighing between 2.0 and 3.0 kg are anesthetized by intramuscular injection of 0.5–0.7 mL/kg rodent cocktail (100 mg/mL ketamine, 20 mg/mL xylazine, and 10 mg/mL acepromazine). Topical anaesthetic drops of proparacaine hydrochloride (0.5% Ophthaine, Bristol-Myers Squibb) are instilled into the animals eye together with drops of cyclopentolate (1%, Cyclogyl®, Alcon, Ft. Worth, Tex.) and phenylephrine (10.0% CibaVision, Duluth, Ga.) to achieve maximal dilation of the pupil. All operations are performed under an operating microscope.

For these experiments, donor corneas are obtained from Fisher rats (Charles River Laboratory, Wilmington, Mass.) weighing approximately 200–300 g. Rats are sacrificed via carbon dioxide asphyxiation. Eyes are enucleated immediately after sacrifice, stored in a modified tissue-culture medium at 4° C. Immediately preceding the xenograft procedure, corneas are excised with sterile scissors and washed with the modified tissue-culture medium. For some experimental procedures, the tissue culture medium is supplemented with a BPI protein product, for pretreatment of the donor tissue prior to transplantation. Corneal buttons that are approximately 2.0 mm are taken by trephination for grafting.

For the transplantation operation, following proptosis of the eye, an incision of approximately 4 mm in length, parallel to and within approximately 6 mm from the superior limbus is made on the cornea. The depth of the incision is approximately on-half the corneal thickness. A peripheral pocket large enough to accommodate the xenograft is made from the incision to within about 2 mm from the superior limbus by additional intrastromal dissection with a cyclo-dialysis spatula. The location of the pocket is made consistent in order to minimize any variable effects arising from different sites of implantation. The pocket is then irrigated with approximately 40 μl of gentamicin sulfate ophthalmic solution, after which the rodent corneal button is implanted and spread as uniformly as possible. The corneal incision is then closed with a 6-0 silk suture. An additional approximately 40 μl dose of gentamicin sulfate ophthalmic solution is applied to the operated eye immediately following the operation. Alternatively, or as an adjunct to gentamicin, a BPI protein product ophthalmic solution is applied to the recipient's eye pre- and/or post-operation.

Postoperatively, all animals receive approximately 40 μl gentamicin sulfate ophthalmic solution (3 mg/mL) daily until the removal of the corneal suture on day 7. Daily post-operative slit-lamp examinations are performed to assess the rate of the clearing of the graft, the progression of the vascularization, and any evidence of uveitis or allograft reaction.

In one study, 4 groups of rabbits undergoing xenograft procedures are treated as follows: (a) 5 rabbits receive a BPI protein product 5 times daily form the day of xenograft procedure for a minimum of 1 month; (b) 5 rabbits receive vehicle control 5 times daily for a minimum of 1 month; (c) 5 rabbits receive prednisolone (1%, Predforte®, Allergan, Irvine, Calif.) 5 times daily for a minimum of i month; and (d) 5 rabbits receive a BPI protein product and 1% prednisolone, each 5 times daily for a minimum of 1 month. In collateral experiments, pretreatment of the graft tissue with a BPI protein product ophthalmic solution is performed prior to implantation. Additionally, a BPI protein product ophthalmic solution is applied to irrigate the pocket and to the operated eye immediately following the operation, alone or as an adjunct to an antimicrobial agent such as gentamicin.

The appearance of one or more of the following clinical signs is used to indicate the onset of the allograft reaction: (1) the clouding of a part or all of the corneal stroma in a graft which had previously been clear; (2) epithelial rejection line; (3) endothelial rejection line, or (4) neovascularization, which is graphed with respect to the affected corneal meridians. Graft survival is recorded in days from the date of surgery until the first day on which any of the listed clinical signs first appear. The progression of the xenograft reaction is observed from several days prior to sacrificing the animal in order to confirm the diagnosis. Rabbits are sacrificed via a lethal dose of somlethol (6 grs./mL). Globes are enucleated and fixed in half-strength Karnovsky's fixative. Sections are stained with hematoxylin and eosin to determine cellular infiltration. Graft rejection scores are analyzed using the Mann-Whitney U test; statistics are performed using Statview SE+Graphics Software (Abicus Concepts, Berkeley, Calif.).

Clinical benefit of administration of BPI protein product with and without co-treatment with corticosteroids is assessed by any delay in the onset of or prevention of clinical signs of allograft reaction or rejection, delay or prevention of corneal neovascularization and/or opacification. Clinical benefit is also assessed by reduction, through prevention or alleviation, of one or more adverse effects and symptoms associated with or resulting from corneal transplantation, including formation of characteristic epithelial or endothelial rejection lines, loss of visual acuity, photophobia, hyperemia, chemosis, iritis, changes in IOP or ocular pain.

Numerous modifications and variations of the above-described invention are expected to occur to those of skill in the art. Accordingly, only such limitations as appear in the appended claims should be placed thereon.

What is claimed is:

1. A method of treating a corneal transplant patient comprising topically administering to the cornea of the patient an amount of a bactericidal/permeability-increasing (BPI) protein product effective to reduce the incidence of transplant rejection or of corneal neovascularization or of corneal opacification.

2. The method of claim 1 wherein the BPI protein product is an amino-terminal fragment of BPI protein.

3. The method of claim 1 wherein the BPI protein product is rBPIhd 21.

4. The method of claim 1 wherein the BPI protein product is a BPI-derived peptide.

5. The method of claim 1 wherein the BPI protein product is $rBPI_{42}$.

6. The method of claim 1 further comprising the step of administering an anti-inflammatory agent or an antimicrobial agent.

7. A method of claim 6 wherein the anti-inflammatory agent is a corticosteroid.

8. The method of claim 6 wherein the antimicrobial agent is an antibiotic selected from the group of ciprofloxacin, gentamicin and ofloxacin.

9. A method for reducing the incidence of corneal transplant rejection or of corneal neovascularization or of corneal opacification comprising application of an effective amount of a BPI protein product to corneal graft tissue prior to transplantation.

* * * * *

UNITED STATES PATENT AND TRADEMARK OFFICE
CERTIFICATE OF CORRECTION

PATENT NO.   :   5,686,414                                    Page 1 of 2

DATED        :   November 11, 1997

INVENTOR(S)  :   Patrick J. Scannon

It is certified that error appears in the above-identified patent and that said Letters Patent is hereby corrected as shown below:

Cover page, Other Publications, delete "Invastigative" and substitute therefor --Investigative--

Cover page, Other Publications, delete "Boisioly" and substitute therefor --Boisjoly--

Cover page, Other Publications, delete "1981" and substitute therefor --1989--

At Col. 1, line 50, delete "cornea/" and substitute therefor --corneal--

At Col. 2, line 1, delete "Cornea/" and substitute therefor --Corneal--

At Col 2, line 47, delete "anti" and substitute therefor --until--

At Col. 4, line 35, delete "mount" and substitute therefor --amount--

At Col. 6, line 3, delete "ofloxaein" and substitute therefor --ofloxacin--

At Col. 6, line 4, delete "neomyein" and substitute therefor --neomycin--

UNITED STATES PATENT AND TRADEMARK OFFICE
CERTIFICATE OF CORRECTION

PATENT NO. : 5,686,414

DATED : November 11, 1997

INVENTOR(S) : Scannon

It is certified that error appears in the above-identified patent and that said Letters Patent is hereby corrected as shown below:

At Col. 6, line 6, delete "vancomyein" and substitute therefor --vancomycin--

At Col. 7, line 18, after the word "about", delete "i" and substitute therefor --1--

At Col. 8, line 9, delete "pelypeptide" and substitute therefor --polypeptide--

At Col. 10, line 26, delete "titrate" and substitute therefor --citrate--

At Col. 11, line 5, delete "dotting" and substitute therefor --clotting--

At Col. 11, line 12, delete "enueleated" and substitute therefor -- enucleated

At Col. 12, line 20, delete "cornea/" and substitute therefor --corneal--

At Col. 13, line 30, after the word "of" delete "i" and substitute therefor "1"

At Col. 21, line 11, delete "rBPIhd21" and substitute therefor --$rBPI_{21}$

Signed and Sealed this

Twentieth Day of October, 1998

Attest:

*Attesting Officer*

BRUCE LEHMAN

*Commissioner of Patents and Trademarks*